(12) United States Patent
Matsumoto (10) Patent No.: US 7,076,027 B2
(45) Date of Patent: Jul. 11, 2006

(54) FLUOROSCOPIC APPARATUS AND METHOD

(75) Inventor: Kazuhiro Matsumoto, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 44 days.

(21) Appl. No.: 10/954,030

(22) Filed: Sep. 29, 2004

(65) Prior Publication Data

US 2005/0084067 A1  Apr. 21, 2005

(30) Foreign Application Priority Data

Oct. 21, 2003  (JP) .............................. 2003-360522

(51) Int. Cl.
*H05G 1/26* (2006.01)
(52) U.S. Cl. ....................... 378/98.8; 378/97
(58) Field of Classification Search ................. 378/62, 378/108–112, 116, 38, 94, 97, 98.8, 98.12
See application file for complete search history.

(56) References Cited

U.S. PATENT DOCUMENTS 5,539,798 A       7/1996  Asahina et al.
6,222,906 B1 *   4/2001  Sakaguchi et al. ......... 378/98.8
6,292,537 B1 *   9/2001  Zimmermann .............. 378/108

FOREIGN PATENT DOCUMENTS

JP           2786849          5/1998

* cited by examiner

*Primary Examiner*—Edward J. Glick
*Assistant Examiner*—Hoon Song
(74) *Attorney, Agent, or Firm*—Morgan & Finnegan LLP (57) ABSTRACT

The object of the present invention is to enable photographing of a desired X-ray image in accordance with each of fluoroscopy, radiography of moving images in an area of interest and spot radiography by simplified operations, and to reduce an exposure dose to a subject. A correlation table is previously input before radiographing (S1), and is memorized (S2). A radiographer sets an irradiation field R to R1 (S3), and an X-ray aperture is opened by predetermined quantity (S4). An opening value is sent to a control part (S5), and X-rays irradiate a subject P on an irradiation condition of a tube voltage (V) and tube current (A) based on the correlation table (S6). The emitted X-rays pass through the subject, enter a planar X-ray-detecting element, then are read and converted to picture signals. In addition, a method of reading picture signals through a reading circuit can be linked to information on the correlation table, and the reading circuit is controlled so as to add picture signals, for instance, of 4 by 4 (=16) pixels which are adjacent to each other into a picture signal of 1 pixel and read it (S7).

3 Claims, 6 Drawing Sheets

FLUOROSCOPIC APPARATUS AND METHOD

BACKGROUND OF THE INVENTION

1. Field of the Invention

The present invention relates to a fluoroscopic apparatus and method for radiographing an image by using a radioactive ray such as an X-ray.

2. Related Background Art

Figure 6:
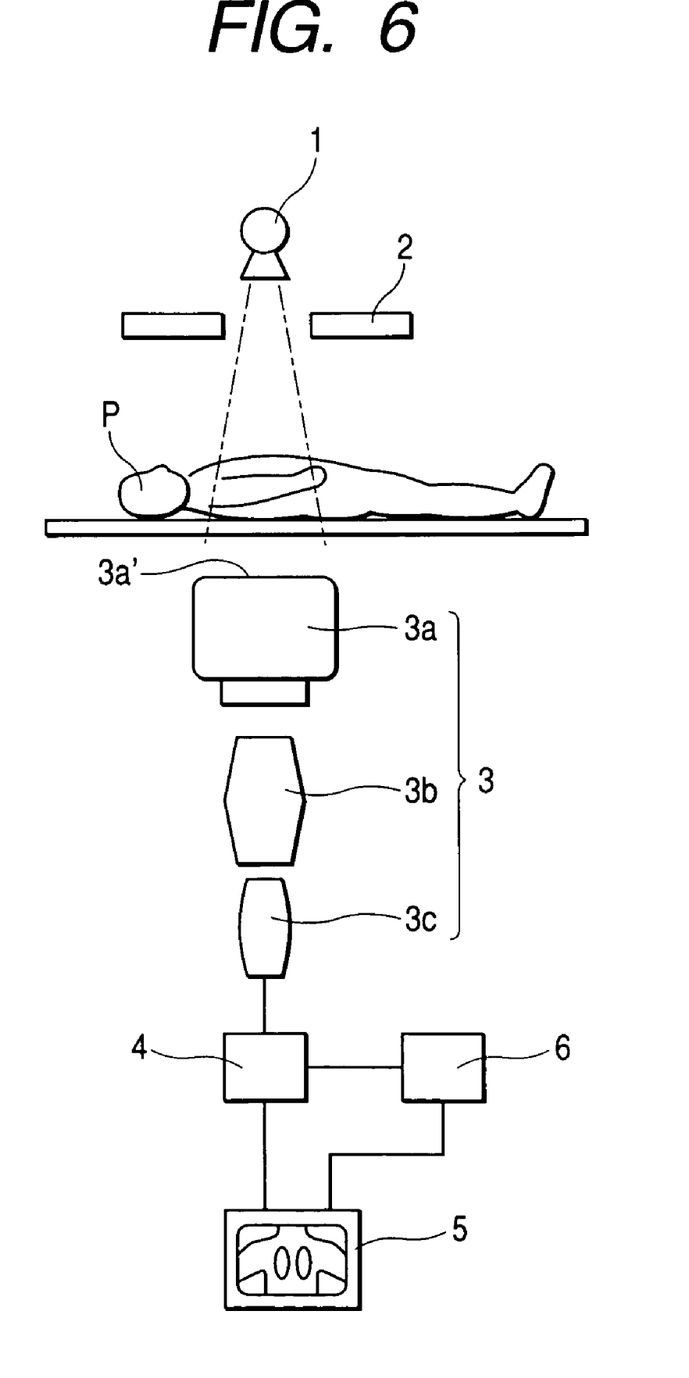
FIG. 6 is a block diagram of a conventional fluoroscopic apparatus.

In the field of diagnostic imaging using a radiographic apparatus, particularly in a fluoroscopic apparatus, an I. I. (an image intensifier)-television system is used widely. More specifically, in the apparatus, as shown in FIG. 6, a subject P is irradiated with X-rays emitted from an X-ray tube 1 through an X-ray aperture 2, the transmitted X-rays which have passed through the subject P, are detected with a detecting unit 3 and are converted to picture signals, and then the converted picture signals are displayed on a monitor 5 as images through image processing means 4.

X-rays to irradiate the subject P, is set so as to irradiate an only the predetermined area required for radiography through the X-ray aperture 2. A detecting unit 3 converts the X-rays having passed through the subject P to an optical image made of visible lights by an I. I. (an image intensifier) 3a, leads the converted optical image to a television camera 3c through an optical system 3b, and converts the optical image to picture signals by the television camera 3c.

Image processing means 4 converts input picture signals to digital picture signals, and carries out various computations such as reduction and enlargement for the images, movement for image positions and calculations of picture signals, and image processing. A recording device 6 records and keeps digital picture signals before and after the image processing, and can keep moving images photographed by continuously or intermittently irradiating a subject P with X-rays, and keep still images photographed at arbitrary timings while the inspector observes the moving images.

An area of a subject P which can be photographed with passing X-rays incident to an input plane 3a' of the I. I. 3a of such a fluoroscopic apparatus, is called a visual field size. The maximum visual field size of the normal I. I. 3a is determined by the diameter of the X-ray aperture, and a settable visual field size is changed stepwise. In radiographing a subject P, the radiographer determines the size of a radiographic area by setting the visual field size.

In addition, by narrowing a visual field size, an enlarged optical image with high resolution can be obtained. A 12-inch wide I. I. 3a can be changed to four sizes, for instance, of 12, 9, 7.5 and 6 inches, and when the visual field size is set to 6 inches, a photograph can be taken in the magnification (resolution) of four times higher than that in 12 inches.

Furthermore, in Japanese Patent Registration No. 2786849, an X-ray diagnostic apparatus is disclosed which can appropriately visualize an X-ray image in accordance with a radiographing portion, and with a fluoroscopic mode or a radiographic mode.

However, the above-described conventional apparatus has the problems described below. In radiography of a subject P, conditions in a fluoroscopy for determining the position of an objective part to be radiographed are desirably a wide area, high sensitivity and a low X-ray dose, while conditions in radiographing a moving image during fluorography or a spot radiography for radiographing still images are desirably high S/N and high resolution. In addition, in either radiography, it is requested that a radiographing area of a subject P can be freely set.

There are many such requests, for instance, when a wide radiographic image is captured in fluoroscopy and then a necessary area for fluoroscopy or spot radiography of an objective part (an area of interest) is going to be specified, in another word, when the quantity of irradiating X-rays for radiography is increased, or a resolution for radiography is increased, in order to obtain clearer images with high S/N, and when the area of interest is pursued while slowly narrowing the photographing area.

In such a case of radiography, the setting of an X-ray irradiation condition and an X-ray aperture and the setting of the visual field size of the I. I. 3a must be independently carried out. But, the above conventional apparatus has a disadvantage in operability.

In addition, a technology is known which synchronizes an irradiated area with X-ray to a visual field size by controlling the opening of the X-ray aperture 2 in accordance with a selected visual field size, when changing the visual field size of the I. I. 3a to a smaller size during fluoroscopy, but according to the technology, the subject is irradiated with unvisualized and useless X-rays while the X-ray aperture 2 is moving.

SUMMARY OF THE INVENTION

An object of the present invention is to provide a fluoroscopic apparatus and method which can take a radiograph with a simplified operation and reduces an exposure dose.

In order to achieve the above object, for example, a fluoroscopic apparatus of the present invention comprises the following arrangement.

That is, a fluoroscopic apparatus comprises X-ray emission means for irradiating a subject with X-rays, narrowing means for limiting an X-ray irradiation range by changing an opening, X-ray image-detecting means for picking up the X-rays which have been emitted from the X-ray emission means and have passed through the subject into the image of picture signals, and control means for controlling the irradiation condition of the X-ray emission means so as to be interlocked with the opening information or irradiation field information of the narrowing means.

In order to achieve the above object, for example, a fluoroscopic apparatus of the present invention comprises the following arrangement.

That is, a fluoroscopic apparatus comprises X-ray emission means for irradiating a subject with X-rays, narrowing means for limiting an X-ray irradiation range by changing an opening, and X-ray image-detecting means for picking up the X-rays which have been emitted from the X-ray emission means and have passed through the subject into the image of picture signals, reading and computing means for reading the picture signals pixel-by-pixel from the X-ray image-detecting means, adding the picture signals of at least one or more pixels and outputting them, and control means for controlling the irradiation condition of the X-ray emission means and an adding method in the reading and computing means so as to be interlocked with the opening information or irradiation field information of the narrowing means.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Preferred embodiments of the present invention will now be described in detail in accordance with the accompanying drawings.

The present invention will be described in detail with reference to embodiments shown in the drawings.

The fluoroscopic apparatus according to the present invention has setting means for previously setting a correlation table including the irradiation condition of X-ray emission means and an adding method, which are controlled so as to be interlocked with the opening information or irradiation field information of narrowing means, wherein control means controls the irradiation condition and the adding method on the basis of the correlation table.

In a fluoroscopic apparatus according to the present invention, the irradiation condition of X-ray emission means includes a tube voltage and a tube current both applied to the X-ray emission means.

In a fluoroscopic apparatus according to the present invention, an adding method depends on the number of pixels to be added.

Embodiment 1

Figure 1:
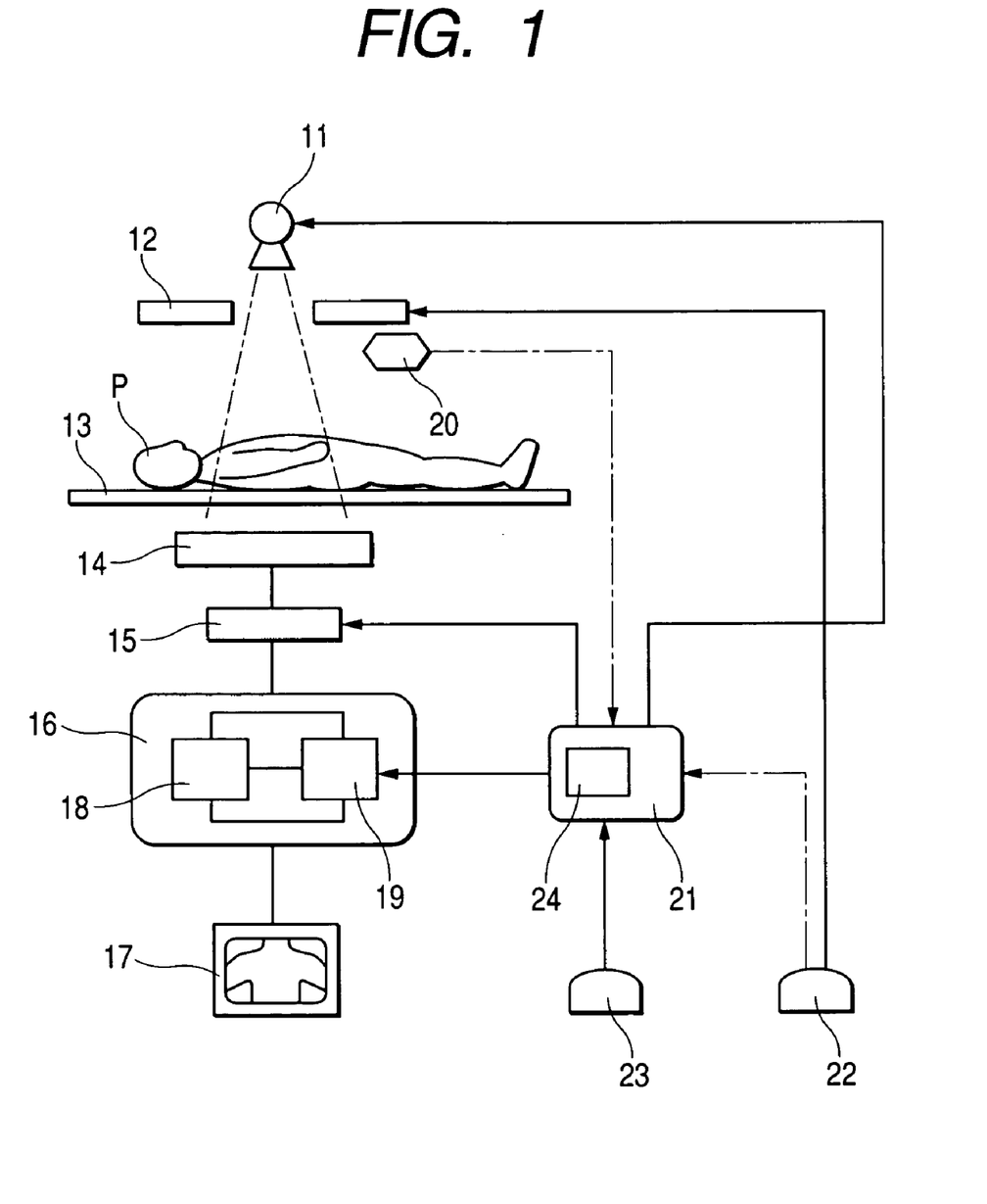
FIG. 1 is a block diagram of a fluoroscopic apparatus in the embodiment 1.

FIG. 1 is a block diagram showing the embodiment 1 of a fluoroscopic apparatus. The fluoroscopic apparatus has sequentially an X-ray aperture 12 for determining an X-ray radiation field, a top plate 13 for mounting a subject P thereon, and a planar X-ray-detecting element 14 for detecting the X-rays having passed through the subject P, disposed in front of an X-ray tube 11 for irradiating the subject P with X-rays.

The output of a planar X-ray-detecting element 14 is sequentially connected to a reading circuit 15 for reading picture signals from the planar X-ray-detecting element 14, an image processing part 16 for image-processing read picture signals, and a display 17 such as a television monitor for visualizing the picture signals. The image processing part 16 has a memory 18 for keeping the picture signals and a computing unit 19 installed in the inside.

In the vicinity of an X-ray aperture 12, opening sensing means 20 for detecting the opening of the X-ray aperture 12 is installed, and the output is connected to a control part 21. In addition, the X-ray aperture 12 is connected with the output of irradiation field setting means 22 for assigning a quantity of the opening, and the output of irradiation field setting means 22 is also connected to the control part 21.

A control part 21 is connected with input means 23 for operating input and assignment of each control parameter associated with radiography, and the control part 21 has a memory 24 installed in the inside. In addition, the output of the control part 21 is connected to an X-ray tube 11, a reading circuit 15 and a computing unit 19. Furthermore, mutual distances in an X-ray irradiation direction between each of the X-ray tube 11, a subject P and a top plate 13, and a planar X-ray-detecting element 14 are fixed during radiography.

Figure 2:
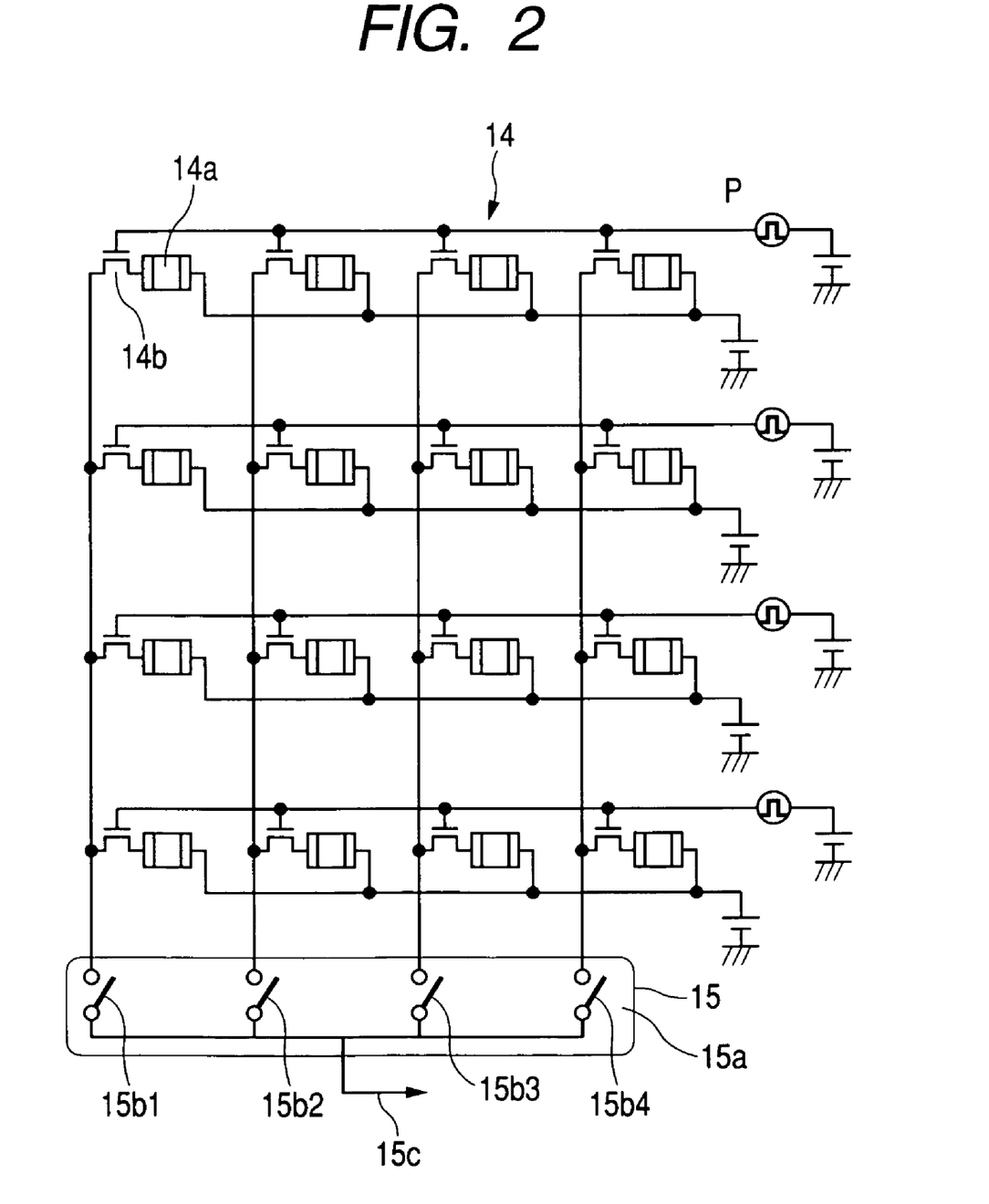
FIG. 2 is a conceptual drawing of a structure and actuation of a planar X-ray-detecting element and a reading circuit.

FIG. 2 is a conceptual drawing showing the structure and actuation of a planar X-ray-detecting element 14 and a reading circuit 15. When X-rays having passed through the subject P are incident on the planar X-ray-detecting element 14, the X-rays are converted to light by a fluorescent screen which is not shown, and converted light generates electric charge according to X-ray intensity in a photoelectric transducing element 14a arranged in a two-dimensional shape. The electric charge is stored in a storage part in a transducing element 14a, and the X-ray image of the subject P is converted into an electric charge distribution with the two-dimensional shape.

Subsequently, a transfer pulse P is transferred to a TFT (a thin-film transistor) of a transfer part 14b installed in each transducing element 14a on the top row, and is input in the transfer part 14b as electric switching signals. Then, the electric charge stored in the transducing element 14a is transferred to the electric switch 15b of a multiplexer 15a of a reading circuit 15 through the transfer part 14b, and is finally sequentially transferred to a signal output terminal 15c by a sequential connection of the electric switch 15b in order of 15b1, 15b2 and so on. Thus the reading of picture signals of one line on the top row is completed.

Read picture signals are converted to digital image data through an amplifier or an analog-to-digital converter which is not shown. Thus, a transfer pulse P from the top row to the bottom row is sequentially sent to a reading circuit 15, while synchronizing with it, each electric switch in 15b of the multiplexer 15a is connected with a signal output terminal 15c sequentially from left to right, thereby the reading is carried out for the picture signals on the whole surface of a planar X-ray-detecting element 14, and the X-ray images are memorized and kept as digital picture signals in the memory 18 of an image processing part 16.

In diagnosis through radiography for a particular part of a subject P, ordinarily, as an exposed area is narrowed, a demand of observation for more detailed images increases. Such an example is the case of radiographing the vicinity of heart, in which it is wanted to specify an interested region such as a neoplasm while narrowing a photographing area from a whole chest image, or to observe more details in the region of an area of interest.

In the present embodiment, a correlation table between a size of a field to be irradiated with X-rays and an X-ray irradiation condition in accordance with a size, resolution and picture quality of a radiographing portion and an exposed area required for a diagnosis, is previously input before radiography and is memorized. The X-ray irradiation conditions are considered to be, for instance, a tube voltage, a tube current, and the pulse width and pulse rate of an intermittent irradiation.

Figure 3:
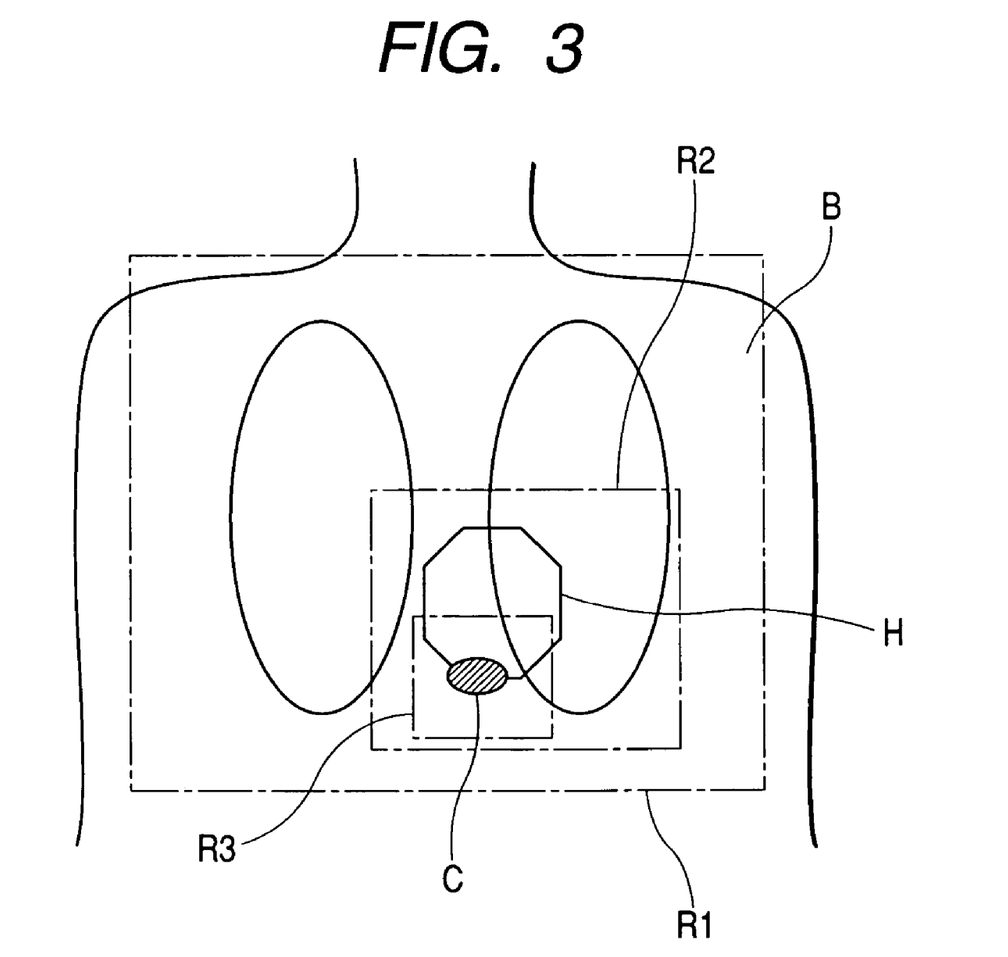
FIG. 3 is an explanatory drawing of a radiographing portion and an irradiation field.

FIG. 3 is an explanatory drawing showing an example of a relation between an exposed portion and a field size. When the field sizes necessary and sufficient for photographing the whole chest B, the vicinity of heart H and the area of interest C of the vicinity of heart H are respectively defined as R1, R2 and R3, and when the whole chest B is going to be radiographed into an image with low resolution, the vicinity of heart H with middle resolution, and the area of interest C with high resolution, a correlation table as shown in Table 1 is set and memorized before radiography. Here, the tube current (A) has a relation of A1<A2<A3.

TABLE 1

| Irradiation field R | Tube voltage (V) | Tube current (A) | Reading/ computing method |
|---|---|---|---|
| R ≦ R3 | V1 | A3 | no addition of pixels |
| R3 < R ≦ R2 | V1 | A2 | addition of 4 pixels |
| R2 < R ≦ R1 | V1 | A1 | addition of 16 pixels |

In the case of the correlation table, because a radiographing portion is limited to the whole chest B, the tube voltage (V) is constant, but the tube current (A) increases as a higher resolution and higher S/N are required to the imaging for an exposed area.

Figure 4:
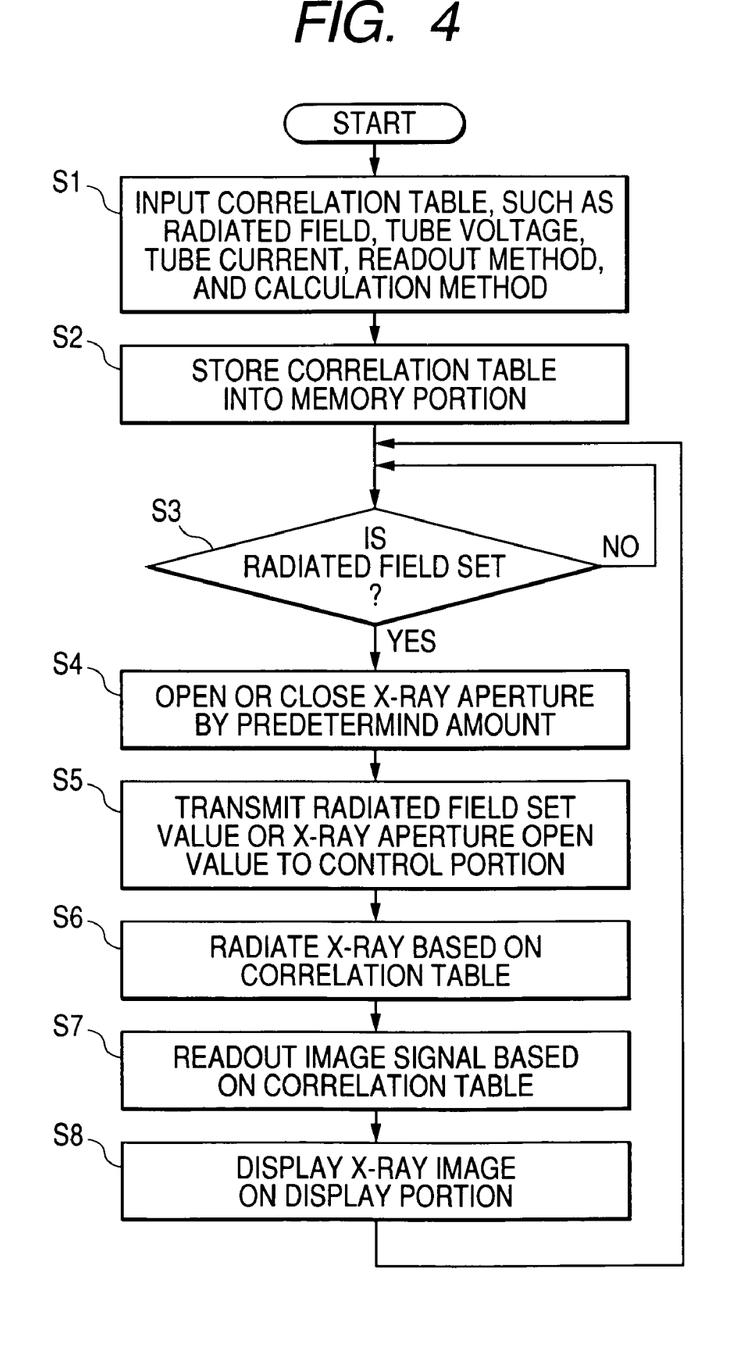
FIG. 4 is a flow chart of the embodiment 1.

FIG. 4 is a flow chart of actuation. First, a correlation table is previously input to input means 23 before radiography (step S1), and is memorized in a memory 24 (step S2). Subsequently when a photographer sets an irradiation field R to R1 by using irradiation field setting means 22 (step S3), an X-ray aperture 12 is automatically opened by predetermined quantity through a drive mechanism which is not shown (step S4). Because relative distances among an X-ray tube 11, a subject P and a planar X-ray-detecting element 14 are constant, the opening quantity of the X-ray aperture 12 is uniquely determined in conjunction with the set size of the irradiation field R. In the setting of the irradiation field R, there is no harm in a manual operation of the X-ray aperture 12.

Concurrently with the setting of an irradiation field R, either the set value by irradiation field setting means 22 or the opening value by opening sensing means 20 is sent to a control part 21 (step S5), and the whole chest B of a subject P is irradiated with X-rays (step S6) under an irradiation condition based on a correlation table in Table 1. In this case, because an exposed portion is the whole chest B, that is to say, a size of an irradiation field is R1, the condition of the third line of the correlation table is applied. Then, the tube voltage (V) of X-rays to be emitted therefrom is a constant value V1 without depending upon a field size R1, but a tube current (A) is a small current A1.

Emitted X-rays pass through the chest of a subject P, enter a planar X-ray-detecting element 14, then are read by a reading circuit 15, and are converted to picture signals. Furthermore, a method of reading picture signals through a reading circuit 15 can be linked to irradiation conditions on the correlation table, as needed. In this case, the control part controls the reading circuit 15 so as to add picture signals of 4 by 4 (=16) pixels which are adjacent to each other into a picture signal of 1 pixel and read it (step S7).

More specifically, transfer pulses P of transducing elements 14a on the four lines of the top row which are adjacent to each other, among transducing elements 14a arranged in a two-dimensional shape which are described in FIG. 2, are simultaneously sent to transfer parts 14b of the transducing elements 14a, and an electric switch signal is input in the TFT which is the transfer part 14b. Then, a picture signal of 4 pixels which are longitudinally adjacent, are simultaneously transferred to the electric switch 15b of a multiplexer 15a. When the four adjacent electric switches 15b are simultaneously connected, the adjacent 16 pixels of picture signals can be simultaneously added and read as one picture signal.

Thus, the simultaneous connection of adjacent four electric switches 15b of the multiplexer 15a are sequentially repeated from left to right, and the reading of the picture signals of every 16 pixels is completed for the top four lines. When the operation is sequentially repeated from the top row to the bottom row, all picture signals can be read as an assembly considering 16 pixels as one picture signal. Thus read picture signals are displayed in a display 17 as an X-ray image of the whole chest B (step S8).

The displayed image where picture signals of 16 pixels adjacent each other are displayed as one picture signal, is an image having low resolution. However, because a tube current A1 passed through an X-ray tube during X-ray irradiation is small, an exposed dose per unit area of a subject P is small, and because the dose of X-rays irradiating adjacent 16 pixels are added and are treated as a one picture signal, the apparent dose of X-rays irradiating one displayed picture signal is about 16 times of one pixel.

As for another case, when a photographer sets an irradiation field R to R2 by using irradiation field setting means 22 (step S3) in order to radiograph the vicinity H of heart, an X-ray aperture 12 is closed by predetermined quantity (step S4). Simultaneously, either the set value by the irradiation field setting means 22 or the opening value according to an opening sensing means 20 is sent to a control part 21 (step S5), and the only vicinity H of heart of a subject P is irradiated with X-rays (step S6) under an irradiation condition based on the correlation table in Table 1. More specifically, a tube voltage (V) is a constant value V1, but a tube current (A) is a middle current A2. Emitted X-rays pass through the only vicinity H of heart of the subject P, enter a planar X-ray-detecting element 14, then are read by a reading circuit 15, and are converted to picture signals.

A reading circuit 15 reads picture signals on the basis of the condition in the second line of the correlation table in Table 1, and is controlled so as to add picture signals of 2 by 2 (=4) pixels which are adjacent to each other into a picture signal of 1 pixel and read it (step S7). More specifically, transfer pulses P of transducing elements 14a on the 2 lines of the top row, which are adjacent to each other among transducing elements 14a, are simultaneously transferred to transfer parts 14b of the transducing elements 14a, and electric switch signals are input to the TFT which is a transfer part 14b. When the two adjacent electric switches 15b of a multiplexer 15a are simultaneously connected, the adjacent 4 pixels of picture signals are simultaneously added and read.

Thus, simultaneous connection of the adjacent two electric switches 15b of the multiplexer 15a are sequentially repeated from left to right, and the reading of the picture signals of every 4 pixels is completed for the top two lines. When the operation is sequentially repeated from the top row to the bottom row, all picture signals can be read as an assembly considering 4 pixels as 1 picture signal.

As described above, picture signals are read and displayed in a display 17 (step S8). A displayed X-ray image in the vicinity H of heart, where picture signals of 4 pixels adjacent each other are displayed as one picture signal, is an image having a middle level of resolution. On the other hand, because the dose of X-rays irradiating adjacent 4 pixels are added and are treated as a one picture signal, the apparent dose of X-rays irradiating one displayed picture signal is about 4 times of one pixel.

As for further another case, when a photographer sets an irradiation field R to R3 by using irradiation field setting means 22 (step S3) in order to radiograph an area of interest C, an X-ray aperture 12 is closed again by predetermined quantity (step S4), and only the area of interest C of the subject P is irradiated with X-rays. At the same time, either the set value by irradiation field setting means 22 or an opening value according to opening sensing means 20 is sent to a control part 21 (step S5), and the X-rays under an irradiation condition based on the first line of the correlation table in Table 1 are emitted (step S6). Specifically, the tube voltage (V) remains a constant value V1, but the tube current (A) is a large current A3.

Emitted X-rays pass through the area of interest C of the subject P, enter a planar X-ray-detecting element 14, then are read by a reading circuit 15, and are converted to picture signals. A reading circuit 15 reads picture signals on the basis of the condition in the correlation table of Table 1, and is controlled so as to read a picture signal of one pixel as one picture signal (step S7), and the read picture signals are displayed in the display 17 (step S8).

The X-ray image of an area of interest C in which the picture signals are read and displayed in the display 17 in the above step, is an image with high resolution, where a picture signal of 1 pixel is displayed as one picture signal, and the apparent dose of X-rays irradiating one displayed picture signal is just the dose of X-ray emitted from the X-ray tube 11.

Embodiment 2

In the embodiment 1, picture signals stored in adjacent transducing elements 14a are added in a reading step, but a picture signal in every transducing element 14a may be individually read and converted to digital picture signals, then the adjacent picture signals may be added in a computing unit 19, and the X-ray pictorial image may be displayed. In addition, if the resolution need not be changed in radiography for each irradiation field R, the correlation table may be set so as to synchronize with only an X-ray tube current (A) in accordance with change of the irradiation field R.

Figure 5:
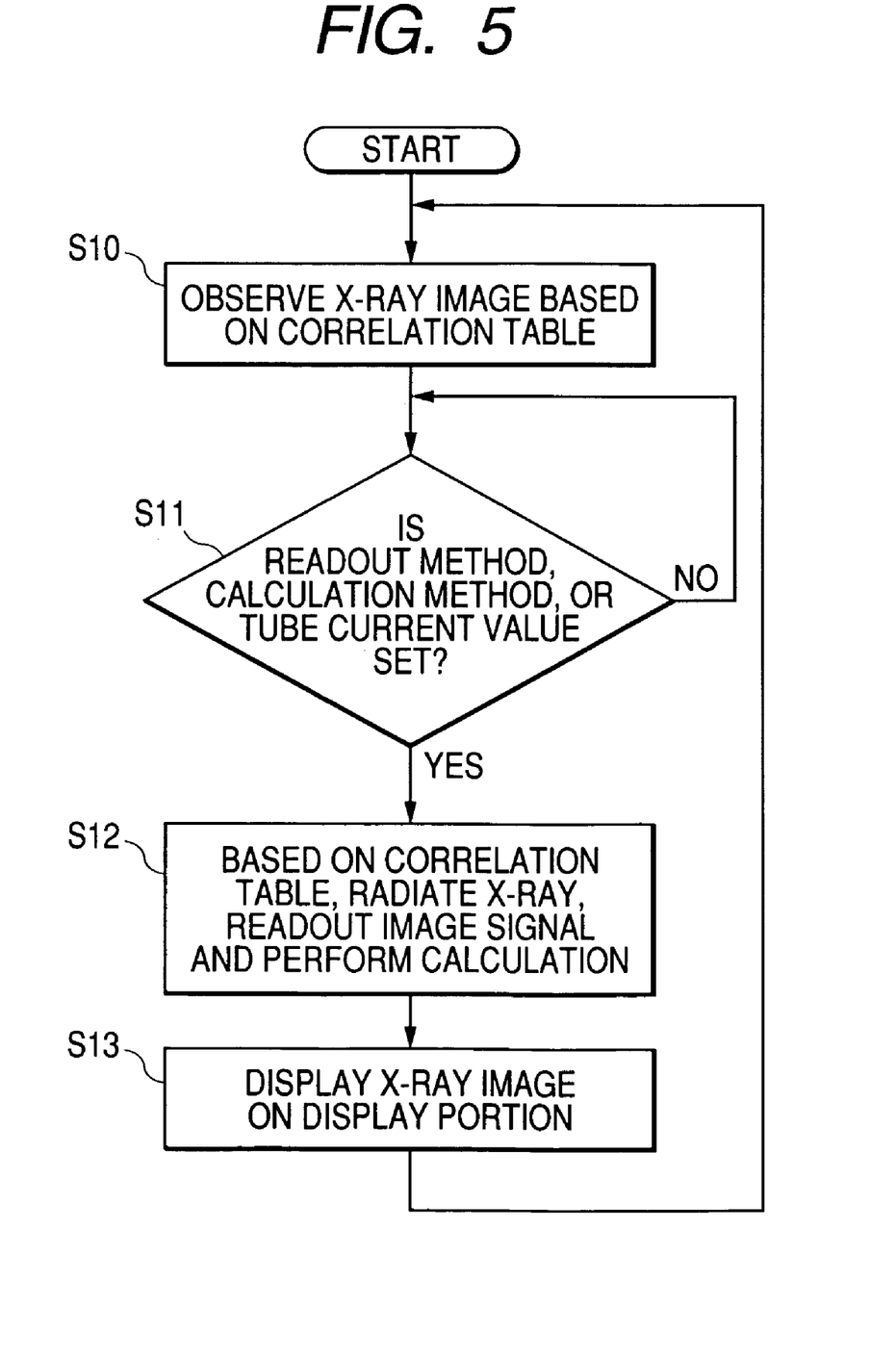
FIG. 5 is an actuation flow chart in the embodiments 2 to 4.

FIG. 5 is a flow chart of the embodiment 2. Table 2 shows a correlation table between a field size and an X-ray irradiation condition in synchronization with a reading or computing method in the embodiment 2.

TABLE 2

| Irradiation field R | Tube voltage (V) | Tube current (A) | Reading/ computing method |
|---|---|---|---|
| R ≦ R3 | V1 | A3 | no addition of pixels |
| R3 < R ≦ R2 | V1 | A2 | addition of 4 pixels |
| R2 < R ≦ R1 | V1 | A3 | no addition of pixels |
|  |  | A2 | addition of 4 pixels |
|  |  | A1 | addition of 16 pixels |

In addition, in a block diagram in FIG. 1, a reading method in a reading circuit 15 or a computing method in a computing unit 19 during fluoroscopy of a subject P can be changed through input means 23.

A radiographic step using a radiographic apparatus having such a configuration is advantageous as follows. For instance, when an irradiation field R1 is set similarly in the case of the embodiment 1, radiography is started under an irradiation condition of a tube voltage (V) of V1 and a tube current (A) of A1 as a default condition, the X-ray image of the whole chest B is observed, in which adjacent 16 pixels are displayed as one picture signal (step S10), and after that when the image of the whole chest B is desired to be observed at higher resolution, for instance, at the resolution of four times higher than the previous resolution, the irradiation field R has to be narrowed into R2 in order to increase the resolution in the embodiment 1.

However, in the present embodiment 2, a reading or computing method is set to "four-pixel addition" by the operation of input means 23 (step S11), then a control part 21 controls the X-ray tube 11 and a reading circuit 15 or a computing unit 19 on the basis of a correlation table in Table 2, a tube current (A) is switched from A1 to A2 while the irradiation field R1 remains unchanged (step S12), and each displayed picture signal is changed to contain adjacent 4 pixels (step S13).

Similarly, when observation at further high resolution is desired, a reading or computing method is set to "no addition of pixel" (step S11), then a tube current (A) is switched from A2 to A3 (step S12), and a picture signal of 1 pixel is displayed as one pixel (step S13). Accordingly, an image with higher resolution can be observed without changing the size of an irradiation field R, and a desired radiographing can be carried out as circumstances demand.

Embodiment 3

Table 3 shows a correlation table between a size of an irradiation field R and a reading or computing method in synchronization with an X-ray irradiation condition in the embodiment 3.

TABLE 3

| Irradiation field R | Tube voltage (V) | Tube current (A) | Reading/ computing method |
|---|---|---|---|
| R ≦ R3 | V1 | A3 | no addition of pixels |
| R3 < R ≦ R2 | V1 | A2 | addition of 4 pixels |
| R2 < R ≦ R1 | V1 | A2 < A ≦ A3 | no addition of pixels |
|  |  | A1 < A ≦ A2 | addition of 4 pixels |
|  |  | A1 | addition of 16 pixels |

In addition, in a block diagram in FIG. 1, the tube current (A) of an X-ray tube 11 can be changed through input means 23 during fluoroscopy of a subject P.

A radiographic step using a radiographic apparatus having such a configuration is advantageous as follows. In a flow chart shown in FIG. 5, for instance, when an irradiation field R1 is set similarly in the case of the embodiment 1, radiography is started under an irradiation condition of a tube voltage (V) of V1 and a tube current (A) of A1 as a default condition, the X-ray image of the whole chest B is observed, in which adjacent 16 pixels are displayed as one picture signal (step S10), and after that when the image of the whole chest B is desired to be observed through a clearer image with higher S/N than the previous one, in the embodiment 1, the irradiation field R has to be narrowed into R2 in order to increase the tube current (A).

However, in the present embodiment 4, the tube current (A) of the X-ray tube 11 is set to a value in a range of A1<A≦A2 (step S11) through the operation of input means 23, then the reading or computing method is switched while an irradiation field R1 remains unchanged (step S12), and each displayed picture signal is changed to contain adjacent 4 pixels (step S13).

Similarly, when clearer observation is desired, the tube current (A) is set to a value in a range of A2<A≦A3 (step S11), then the reading or computing method is switched again (step S12), and a picture signal of 1 pixel is displayed as one pixel (step S13). Accordingly, an image with higher resolution and higher S/N can be observed without changing the size of an irradiation field R, and a desired radiographing can be carried out as circumstances demand.

INDUSTRIAL APPLICABILITY

In the embodiments, a planar X-ray-detecting element 14 is composed so as to directly convert X-ray intensity to electric charge, but there is no harm in using other detecting elements, for instance, a detecting element which has a fluorescent substance layered on the entire surface so as to convert an X-ray intensity to a visible light, and converts the optical intensity further to an electric charge.

In addition, each control parameter and the value in a correlation table which links to an irradiation condition of an X-ray tube 11 in synchronization with the opening information or irradiation field information of narrowing means 12, to a method for reading an image information from the planar X-ray-detecting element 14, and an adding method for the image information read from adjacent pixels, are not limited to the embodiments described above, and can be freely set in accordance with a desired X-ray image required for the purpose of radiography and diagnosis. According to a fluoroscopic apparatus and method according to the present invention, a desired X-ray image in accordance with each of fluoroscopy, radiography of moving images in an area of interest and spot radiography can be photographed by simplified operations.

In addition, because a field size can be arbitrarily set by changing the opening of an X-ray aperture, a useless X-ray irradiation outside an exposed area to be visualized, which is caused by a delay of a movement of the X-ray aperture, can be prevented.

Furthermore, an exposure period is shortened by simplification of operations during radiography, and an exposure dose to a subject can be reduced.

As described above, the present invention can provide a fluoroscopic apparatus and method which can take a radiograph with simplified operations and can reduce an exposure dose.

It is needless to say that the object of the present invention is also achieved by supplying a recording medium (or a storage medium) that records a program code of software which realizes the functions of the above described embodiments, to a system or an apparatus, and making the computer (or CPU or MPU) of the system or the apparatus read and carry out the program code stored in the recording medium. In this case, the program code read from the recording medium by itself realizes the functions of the above-mentioned embodiments, and the recording medium which records the program code constitutes the present invention.

In addition, it is needless to say that the present invention includes not only the case in which the functions of the above described embodiments are realized by the execution of a program code read by a computer, but also the case in which the functions of the above described embodiments are realized by treatment by an operating system (OS) or the like operating on the computer which carries out one or all of actual treatment on the basis of directions from the program code.

It is also needless to say that the present invention includes the case in which the program code read from a recording medium is written on a functionality expansion card inserted to a computer or a memory installed in a functionality expansion unit connected to the computer, and then a CPU mounted on the functionality expansion card or the functionality expansion unit carries out one or all of the actual treatment on the basis of directions of the program code, and the functions of the above described embodiments are realized by the treatment.

When the present invention is applied to the above-described recording medium, the program code corresponding to the flow chart described above shall be stored in the recording medium.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2003-360522 filed on Oct. 21, 2003, which is hereby incorporated by reference herein.

What is claimed is:

1. A fluoroscopic apparatus comprising:
   X-ray emission means for irradiating a subject with X-rays;
   narrowing means for limiting an X-ray irradiation range by changing an opening;
   X-ray image detecting means for picking up the X-rays which have been emitted from the X-ray emission means and have passed through the subject into the image of picture signals;
   reading and computing means for reading the picture signals pixel-by-pixel from the X-ray image detecting means, adding picture signals of at least one or more pixels and outputting them; and
   control means for controlling an irradiation condition of the X-ray emission means and adding method in the reading and computing means so as to be interlocked with an opening information of the narrowing means, wherein the control means decreases current flow into a tube of the X-ray emission means and increases a number of pixels to be added, in accordance with an increment of a size of a field to be irradiated with X-rays.

2. The fluoroscopic apparatus according to claim 1, wherein the irradiation condition of the X-ray emission means includes the tube voltage and a tube current both applied to the X-ray emission means.

3. A fluoroscopic method of an fluoroscopic apparatus which has X-ray emission means for irradiating a subject with X-rays, narrowing means for limiting an X-ray irradiation range by changing an opening, and X-ray image detecting means for picking up the X-rays which have been emitted from the X-ray emission means and have passed through the subject into the image of picture signals, comprises the steps of:
   a reading and computing step of reading picture signals pixel by pixel from the X-ray image detecting means, adding the picture signals read from at least one or more adjacent pixels, and outputting them; and a controlling step of controlling the irradiation condition of the X-ray emission means and the adding method in the reading and computing step so as to be interlocked with an opening information of the narrowing means, wherein the controlling step decreases current flow into a tube of the X-ray emission means and increases a number of pixels to be added, in accordance with an increment of a size of a field to be irradiated with X-rays.

* * * * *

UNITED STATES PATENT AND TRADEMARK OFFICE
CERTIFICATE OF CORRECTION

PATENT NO. : 7,076,027 B2  Page 1 of 1
APPLICATION NO. : 10/954030
DATED : July 11, 2006
INVENTOR(S) : Kazuhiro Matsumoto It is certified that error appears in the above-identified patent and that said Letters Patent is hereby corrected as shown below:

Column 10, Line 55, before "fluoroscopic", change "an" to --a--.

Signed and Sealed this

Seventh Day of November, 2006

JON W. DUDAS
*Director of the United States Patent and Trademark Office*